(12) United States Patent
Boyer et al.

(10) Patent No.: US 8,101,810 B2
(45) Date of Patent: Jan. 24, 2012

(54) REFORMATE BENZENE REDUCTION VIA ALKYLATION

(75) Inventors: Christopher C. Boyer, Houston, TX (US); Lawrence A. Smith, Jr., Pasadena, TX (US); Arvids Judzis, Jr., Houston, TX (US); John R. Adams, Salem, OR (US)

(73) Assignee: Catalytic Distillation Technologies, Pasadena, TX (US)

( * ) Notice: Subject to any disclaimer, the term of this patent is extended or adjusted under 35 U.S.C. 154(b) by 720 days.

(21) Appl. No.: 12/195,118

(22) Filed: Aug. 20, 2008

(65) Prior Publication Data
US 2010/0048970 A1  Feb. 25, 2010

(51) Int. Cl.
C07C 2/52  (2006.01)

(52) U.S. Cl. ..................................... 585/446
(58) Field of Classification Search .................. 585/446
See application file for complete search history.

(56) References Cited

U.S. PATENT DOCUMENTS

| | | |
|---|---|---|
| 4,371,714 A | 2/1983 | Young |
| 4,469,908 A | 9/1984 | Burress |
| 4,849,569 A | 7/1989 | Smith, Jr. |
| 4,882,040 A | 11/1989 | Dessau et al. |
| 5,055,627 A | 10/1991 | Smith, Jr. et al. |
| 5,080,871 A | 1/1992 | Adams et al. |
| 5,118,872 A | 6/1992 | Smith, Jr. et al. |
| 5,118,897 A | 6/1992 | Khonsari et al. |
| 5,196,574 A | 3/1993 | Kocal |
| 5,210,348 A | 5/1993 | Hsieh et al. |
| 5,252,197 A * | 10/1993 | Alexander et al. ............ 208/134 |
| 5,273,644 A | 12/1993 | Wegerer |
| 5,347,061 A * | 9/1994 | Harandi et al. ............... 585/323 |
| 5,446,223 A | 8/1995 | Smith, Jr. |
| 5,476,978 A | 12/1995 | Smith, Jr. et al. |
| 5,756,872 A | 5/1998 | Smith, Jr. et al. |
| 6,315,964 B1 | 11/2001 | Knifton et al. |
| 6,617,481 B1 | 9/2003 | Kulprathipanja et al. |
| 6,855,855 B2 | 2/2005 | Van Den Brink et al. |
| 7,071,369 B2 | 7/2006 | Pohl |
| 7,074,978 B2 | 7/2006 | Pohl |
| 7,253,331 B2 | 8/2007 | Martens et al. |

FOREIGN PATENT DOCUMENTS

EP  0521554 A2  1/1993

OTHER PUBLICATIONS

International Search Report and Written Opinion issued Aug. 31, 2010 in corresponding PCT Application No. PCT/US2009/044423 (8 pages).

* cited by examiner

Primary Examiner — Thuan Dinh Dang
(74) Attorney, Agent, or Firm — Osha • Liang LLP

(57) ABSTRACT

A process for reformate benzene reduction, the process including: feeding a light reformate fraction, an olefin feed, and an alkylation catalyst to an alkylation reaction zone; contacting the light reformate fraction and the olefin feed in the presence of the alkylation catalyst in the alkylation reaction zone to convert at least a portion of the benzene and the olefin to a monoalkylate; recovering a catalyst fraction from an alkylation reaction zone effluent; and recovering a light reformate product having a reduced benzene content.

21 Claims, 2 Drawing Sheets

REFORMATE BENZENE REDUCTION VIA ALKYLATION

BACKGROUND OF DISCLOSURE

1. Field of the Disclosure

Embodiments disclosed herein relate generally to reduction of benzene content in a reformate stream. More specifically, embodiments disclosed herein relate to reduction of benzene concentrations in a reformate stream via alkylation. More specifically still, embodiments disclosed herein relate to reactive distillation for the alkylation of benzene with an olefin in presence of a heterogeneous slurry catalyst that can be continuously regenerated and replaced during operation.

2. Background

The demand for cleaner and safer transportation fuels is becoming greater every year. Reformate, a product of catalytic reforming, is one of the major sources of feedstock for gasoline blending. However, reformate presents a problem meeting strict environmental and health regulations. For example, light reformate typically contains unacceptably high levels of benzene, a known carcinogen.

Refiners in the U.S. and other countries are required to remove benzene from the reformate stream prior to gasoline blending. Practical options to date include extraction, hydrogenation, transalkylation, and alkylation. Each of these options presents challenges, especially to a small or non-integrated refiner, from both a standpoint of cost and feasibility.

Extraction of benzene requires expensive capital investment in necessary equipment and a customer for the benzene product, neither of which may be feasible for a small non-integrated refiner. Also, while it is possible to extract benzene from the gasoline pool by fractionation techniques, such techniques are not preferred, because the boiling point of benzene is too close to that of some of the more desirable organic components, including $C_6$ paraffins and isoparaffins. Monoalkylate aromatics (monoalkylate), such as toluene and xylenes, are more desirable for gasoline blending, as opposed to benzene, because they are less objectionable both from an environmental and a safety point of view.

Alternatively, benzene in reformate may be removed via hydrogenation. However, hydrogenation of aromatics, such as benzene, toluene, and xylenes, results in reduced octane rating of the reformate stream, and thus diminishes the overall value of the fuel. As with extraction, hydrogenation of benzene also may not feasible for a small refiner due to potentially uneconomical costs associated with supplying hydrogen.

Transalkylation of benzene in reformate with polyalkylate to form monoalkylate product is another option available to refiners. Transalkylation may be feasible when a significant source of polyalkylate is readily available. For example, depending on the catalytic reformer operation, the heavy reformate may contain an adequate amount of polyalkylate to facilitate transalkylation of benzene in the light reformate. Polyalkylate typically is not a desired product of catalytic reforming, because of certain restrictions on its content in gasoline. If the polyalkylate content in reformate is insufficient and there is no alternative polyalkylate source available, transalkylation may not be a feasible option to reduce the benzene content in light reformate. Even if polyalkylate feed is readily available, it may still be more economical to reduce benzene in light reformate via alkylation instead of transalkylation.

As described in U.S. Pat. Nos. 4,371,714 and 4,469,908, alkylation of aromatics, such as benzene, is a more mature and better developed technology than transalkylation. The benzene content in light reformate may be reduced by alkylation with an olefin to produce monoalkylate product. Olefinic feed may be available as certain low-value refinery streams, for example, the fluidized catalytic cracker (FCC) off-gas. If an olefin feed is available, its fuel value and the fuel value of the benzene-containing light reformate stream may be upgraded via alkylation, wherein an olefin combines with benzene to form a high-octane value monoalkylate. A typical benzene transalkylation reaction is shown below:

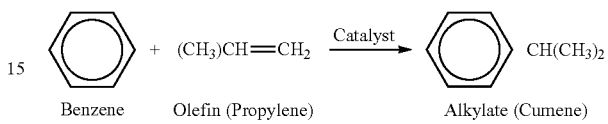

Older alkylation technology, still widely employed in the petrochemical industry, involves the use of a catalyst based on phosphoric acid. As disclosed in U.S. Pat. No. 5,446,223, alkylation reactions may instead utilize non-polluting, non-corrosive, regenerable materials, such as zeolitic molecular sieve catalysts. U.S. Pat. Nos. 4,371,714 and 4,469,908 disclose straight pass alkylation and transalkylation of aromatic compounds using zeolitic molecular sieve catalysts in fixed beds.

A major problem with alkylation of benzene in reformate using a zeolitic catalyst is rapid deactivation of the catalyst due to coking and poisoning, each of which may result in frequent unplanned unit shut downs or other process interruptions, such as for thermal regeneration of the catalyst. U.S. Pat. No. 5,118,897 further discloses a process for reactivating the zeolitic alkylation catalyst by temporary substitution of the olefin supply stream with a hydrogen stream under certain conditions to shorten the thermal catalyst regeneration cycle.

The catalyst deactivation rate due to coking or poisoning may be reduced by maintaining the zeolitic catalyst in at least a partial liquid phase, such as a hydrocarbon slurry. U.S. Pat. Nos. 5,080,871 and 5,118,872 disclose a moving bed reactor for alkylation and transalkylation of aromatic compounds, in which a slurry is produced by adding solid catalyst to the aromatic feed stream and is circulated through the reactor.

One advantage of a moving bed catalyst slurry reactor, as taught by U.S. Pat. Nos. 5,080,871 and 5,118,872, is that the catalyst may be continuously replaced and regenerated during operation, thus reducing the need for additional unit shut downs. The ability to remove deactivated catalyst on-line eliminates the need to remove catalyst poisons from the feeds or regenerate the catalyst in a fixed bed reactor, thus reducing the cost of the benzene removal unit.

To date, benzene removal by alkylation has not been found economical, because of the high capital equipment cost, including new catalyst regeneration facilities. Therefore, there is still a significant need in the art for improved and cost-efficient methods to reduce benzene in reformate streams, especially for smaller refining operations.

SUMMARY OF THE DISCLOSURE

In one aspect, embodiments disclosed herein relate to a process for reformate benzene reduction, the process including: feeding a light reformate fraction, an olefin feed, and an alkylation catalyst to an alkylation reaction zone; contacting the light reformate fraction and the olefin feed in the presence of the alkylation catalyst in the alkylation reaction zone to convert at least a portion of the benzene and the olefin to a monoalkylate; recovering a catalyst fraction from an alkylation reaction zone effluent; and recovering a light reformate product having a reduced benzene content.

In another aspect, embodiments disclosed herein relate to a process for reformate benzene reduction, the process including: feeding a light reformate comprising benzene, an olefin, and an alkylation catalyst to a catalytic distillation column reactor comprising an alkylation reaction zone; concurrently in the catalytic distillation column reactor: contacting the benzene and an olefin in the presence of the alkylation catalyst to convert at least a portion of the benzene and the olefin to a monoalkylate and at least one of a polyalkylate and an olefin oligomer; separating the light reformate comprising the monoalkylate from the catalyst and a heavy components comprising at least one of the polyalkylate and the olefin oligomer; recovering the heavy components and the alkylation catalyst from the catalytic distillation column as a second bottoms fraction; recovering the light reformate having a reduced benzene content from the catalytic distillation column as a second overheads fraction; feeding the second bottoms fraction to a separation zone for separating a liquid fraction comprising at least one of the polyalkylate and the olefin oligomer from a catalyst fraction comprising the catalyst; and feeding the liquid fraction from the separation zone to the first fractionation zone.

In another aspect, embodiments disclosed herein relate to a process for reformate benzene reduction, the process including: feeding a light reformate comprising benzene, an olefin-containing feed, and an alkylation catalyst to a flow reactor comprising an alkylation reaction zone; contacting the benzene and the olefin in the presence of the alkylation catalyst in the alkylation reaction zone to convert at least a portion of the benzene and the olefin to a monoalkylate and at least one of the polyalkylate and an olefin oligomer; recovering an effluent from the flow reactor comprising monoalkylate, light reformate, and the at least one of a polyalkylate and an olefin oligomer; feeding the effluent to a separation zone for separating a liquid fraction, comprising the light reformate, monoalkylate, and the at least one of a polyalkylate and an olefin oligomer, from a catalyst fraction; and recovering the liquid fraction as a light reformate stream having a reduced benzene content.

Other aspects and advantages will be apparent from the following description and the appended claims.

DETAILED DESCRIPTION

Figure 1:
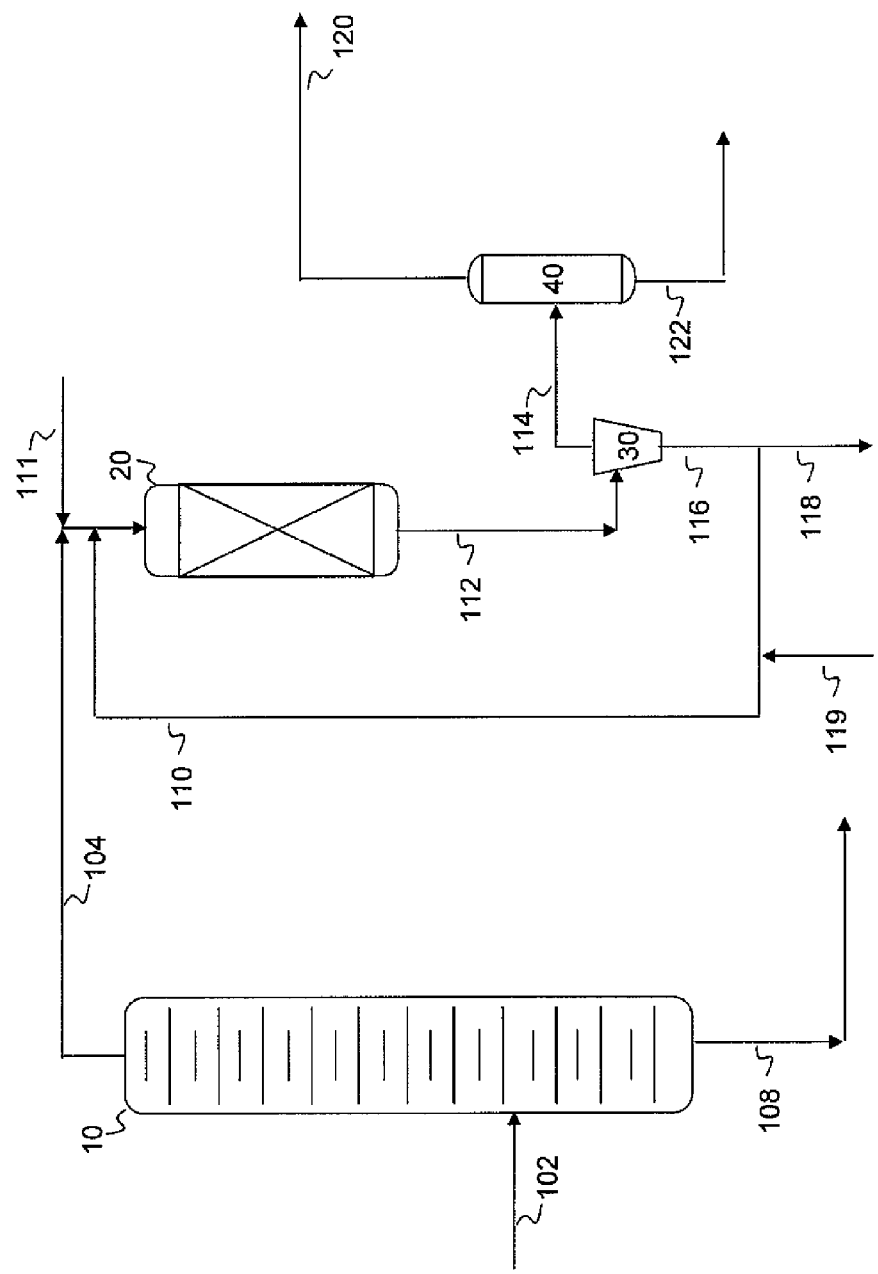
FIG. 1 is a simplified flow diagram of an alkylation process according to embodiments disclosed herein.

Embodiments disclosed herein relate generally to processes for the reduction of benzene content in a reformate stream. More specifically, embodiments disclosed herein relate to reduction of benzene concentrations in a reformate stream via alkylation. More specifically still, embodiments disclosed herein relate to reactive distillation for the alkylation of benzene with an olefin in presence of a heterogeneous slurry catalyst that can be continuously regenerated and replaced during operation.

In embodiments of the processed for reformate benzene reduction disclosed herein, a light reformate stream including benzene may be contacted with an olefin in the presence of an alkylation catalyst to form monoalkylate. In some embodiment, a heterogeneous slurry catalyst may be used to facilitate the alkylation reaction. For the purpose of illustration, several representative alkylation reactions of olefins with benzene are provided as follows:
 1) ethylene+benzene→ethylbenzene
 2) propylene+benzene→propylbenzene
 3) butene+benzene→butylbenzene Processes disclosed herein may be used to reduce the benzene concentration in any number of benzene-containing hydrocarbon streams commonly found in a refinery. In some embodiments, hydrocarbon feeds to the processes disclosed herein may include a full range reformate. Catalytic reforming is a process in which hydrocarbon molecules are rearranged, or reformed in the presence of a catalyst. The molecular rearrangement results in an increase in the octane rating of the feedstock. For example, $C_6$ and $C_7$ paraffin components in a feed may be converted into aromatics and recovered as a reformate product, wherein the conversion may be highly selective towards aromatics production. Naphtha reforming may also be utilized for production of benzene and monoalkylate aromatics. One example of a catalytic reforming process is disclosed in U.S. Pat. No. 4,882,040, among others.

Monoalkylate aromatics in the resulting reformate, such as toluene, ethylbenzene, cumene, and the like, are highly desirable for gasoline feedstock. To the contrary, benzene must be removed from reformate in order to meet the stringent environmental and safety regulations.

Reformate streams may include, for example, up to about 25 weight percent benzene or more, depending upon the feedstock reformed and the reforming process used. Processes disclosed herein may be used to reduce the benzene in the feed to less than 1 weight percent in some embodiments; less than 0.5 weight percent in other embodiments; less than 0.25 weight percent in other embodiments; less than 0.1 weight percent in other embodiments; less than 500 ppm by weight in other embodiments; less than 250 ppm by weight in other embodiments; less than 100 ppm by weight in other embodiments; less than 50 ppm by weight in other embodiments; less than 10 ppm by weight in other embodiments; and less than detectable limits in yet other embodiments. Additionally, processes disclosed herein may result in minimal or no loss of existing monoalkylate (toluene, ethylbenzene, cumene, etc.) present in the reformate feed.

Reduction of benzene content in a reformate stream according to embodiments disclosed herein may be performed by fractionating a full range reformate into a light reformate, including the benzene, and a heavy reformate, including toluene and other existing monoalkylate products in the reformate stream. The light reformate may then be contacted with an olefin in the presence of an alkylation catalyst to convert at least a portion of the benzene to an alkylate product, which may include monoalkylate and polyalkylate. Additionally, olefins may react with themselves under alkylation conditions to form olefin oligomers.

Depending on the reformer feedstock, the full range reformate product may include one or more of benzene, monoalkylate, and polyalkylate. In one embodiment, preliminary separation of the full range reformate may be accomplished using traditional fractional distillation, wherein the benzene in a light reformate may be separated from a heavy reformate. The light reformate comprising benzene may be recovered to further undergo benzene removal. For example, benzene may be removed from the reformate by contacting it with an olefin in presence of an alkylation catalyst.

In one embodiment, olefins useful for the alkylation of benzene may include $C_2$ to $C_5$ olefins. The corresponding alkylation products may include at least one of ethylbenzene, cumene, butylbenzene, and pentylbenzene. In other embodiment, a $C_6$ to $C_8$ olefin may be used. However, alkylation products of some heavy olefins may require removal from the resulting reformate in order to meet an end-point specification for gasoline blending.

Olefins may be supplied from any number of refinery streams. Depending on the availability of an olefin source near an alkylation unit and the relative amount of olefin required for alkylation, one or more different olefin sources may be used. In one embodiment, the olefin feed to the alkylation unit may include a purified olefin feed, such as a 90+ percent propylene stream. In another embodiment, the olefin feed may include a fluidized catalytic cracker (FCC) off-gas including olefins and other light components. When an FCC off-gas is used instead of a purified olefin as the olefin feed, additional back-end separation may be required to isolate the reformate product having a reduced benzene content.

Not all olefins exhibit the same alkylation properties. For example, the alkylation rate of a $C_2$ olefin is much slower than that of $C_3$ and higher olefins. Therefore, if a mixture of olefins is used, the $C_3$ and higher olefins may react nearly to completion, while the $C_2$ olefin (ethylene) may pass through mostly unreacted. As disclosed in U.S. Pat. No. 5,756,872, alkylation may be used to produce a concentrated ethylene stream by reacting $C_3$ and higher olefins within a mixed olefin stream.

An olefin feed may also include certain impurities, for example, light components, dienes, acetylenes, water, sulfur compounds or nitrogen compounds. Some of the impurities may be removed upstream of the alkylation reaction to prevent rapid catalyst deactivation. Other impurities in the olefin feed, such as light components in an FCC off-gas, may be removed downstream of the alkylation reaction along with unreacted olefin. One advantage of using an existing FCC off-gas as an olefin supply, especially for a small refiner, is that the FCC off-gas may be used as either a primary or a supplemental olefin feed to the alkylation reactor in order to remove benzene from the light reformate, thus integrating the units and providing an outlet for the smaller molecules.

The alkylation catalyst used may be such that the size of the catalyst particles is small enough to be suspended in the reformate, either prior to or within the alkylation reaction zone. The catalyst particles may also be large enough to facilitate catalyst separation from the alkylation reactor effluent using conventional separation techniques, such as settling, cyclone separations, and filtration. For example, the catalyst particle size may be in the range from about 5 microns to about 500 microns. In some embodiments, the catalyst particle size may be within the range from about 20 microns to about 200 microns.

As disclosed in U.S. Pat. Nos. 5,476,978, 5,446,223, 5,273,644, 5,118,872, 5,055,627, and 4,849,569, solid acid catalyst, including, but not limited to, zeolitic catalysts and solid inorganic acid catalysts may be used for the alkylation of aromatic hydrocarbons, in particular for alkylation of benzene, for their superior activity and selectivity. The catalyst particles may be suspended directly in the liquid reformate feed stream to the alkylation reactor or may be carried into the reactor as a separate phase. The concentration of catalyst in the slurry may vary over a wide range, depending on such process variables as the catalyst particle size, particle density, surface area, olefin feed rate, ratio of aromatic to olefin, temperature and catalyst activity. The competing considerations of reactivity and physical dynamics of the reactants in a particular system may necessitate adjustment of several variables to approach a desired result.

Zeolites useful in embodiments disclosed herein may include natural and synthetic zeolites. Acidic crystalline zeolitic structures useful in embodiments disclosed herein may be obtained by the building of a three dimensional network of $AlO_4$ and $SiO_4$ tetrahedra linked by the sharing of oxygen atoms. The framework thus obtained contains pores, channels and cages or interconnected voids. As trivalent aluminum ions replace tetravalent silicon ions at lattice positions, the network bears a net negative charge, which must be compensated for by counterions (cations). These cations are mobile and may occupy various exchange sites depending on their radius, charge or degree of hydration, for example. They can also be replaced, to various degrees, by exchange with other cations. Because of the need to maintain electrical neutrality, there is a direct 1:1 relationship between the aluminum content of the framework and the number of positive charges provided by the exchange cations. When the exchange cations are protons, the zeolite is acidic. The acidity of the zeolite is therefore determined by the amount of proton exchanged for other cations with respect to the amount of aluminum.

Alkylation catalysts that may be used in some embodiments disclosed herein may include zeolites having a structure type selected from the group consisting of BEA, MOR, MTW, and NES. Such zeolites include mordenite, ZSM4, ZSM-12, ZSM-20, offretite, gmelinite, beta, NU-87, and gottardite. Clay or amorphous catalysts including silica-alumina and fluorided silica-alumina may also be used. Further discussion of alkylation catalysts may be found in U.S. Pat. Nos. 5,196,574; 6,315,964 and 6,617,481. Various types of zeolitic catalysts may be used for alkylation as well as other types of catalytic refinery processes. FCC processes may utilize at least one of a type Y, Beta, and ZSM-5, for example. The FCC zeolitic catalyst typically contains three parts: the zeolite, typically about 30 to 50 wt. % of the catalyst particle, an active matrix, and a binder. In one embodiment, the particle size of the FCC catalyst may be between 50 and 60 microns. In another embodiment, the zeolitic catalyst may initially come in ammonium form, which may be converted to the $H^+$ form by heating at over 300° C. before being used as an alkylation catalyst. One must take care not to overheat the catalyst prior to alkylation, because excessive temperature may dealuminate the zeolite and shrink the ring structures, which may reduce the activity for alkylation. In addition to zeolitic catalyst, inorganic catalyst, such as sulfated zirconia or tungstated zirconia, may be used for alkylation as well.

In some embodiments, suitable catalysts for alkylation and transalkylation may include metal stabilized catalysts. For example, such catalysts may include a zeolite component a metal component, and an inorganic oxide component. The zeolite may be a pentasil zeolite, which include the structures of MFI, MEL, MTW, MTT and FER (IUPAC Commission on Zeolite Nomenclature), MWW, a beta zeolite, or a mordenite. The metal component typically is a noble metal or base metal, and the balance of the catalyst may be composed of an inorganic oxide binder, such as alumina. Other catalysts having a zeolitic structure that may be used in embodiments disclosed herein are described in U.S. Pat. No. 7,253,331, for example.

Certain zeolitic catalyst that may be used in an FCC reactor may also be used in an alkylation reactor according to embodiments disclosed herein. In one embodiment, a fresh MWW type zeolitic catalyst may be used to facilitate aromatics alkylation, and when spent, it may be further fed to an FCC unit as an equilibrium catalyst. In another embodiment, an FCC catalyst may be fed to an alkylation reactor as make-up catalyst.

One advantage of using FCC catalyst for benzene alkylation is that the catalyst can be used without any added catalyst cost to the refinery. For example, using the FCC catalyst regeneration facilities instead of providing new regeneration facilities for the alkylation unit may provide significant capital cost savings, especially for a small refiner.

In addition to the monoalkylate product, an alkylation reaction may yield other undesirable byproducts in the form of heavy components, comprising one or more of polyalkylate and olefin oligomers. If heavy components are formed during alkylation, additional steps may be implemented to further separate the light reformate product having a reduced benzene content from the heavy components.

Figure 2:
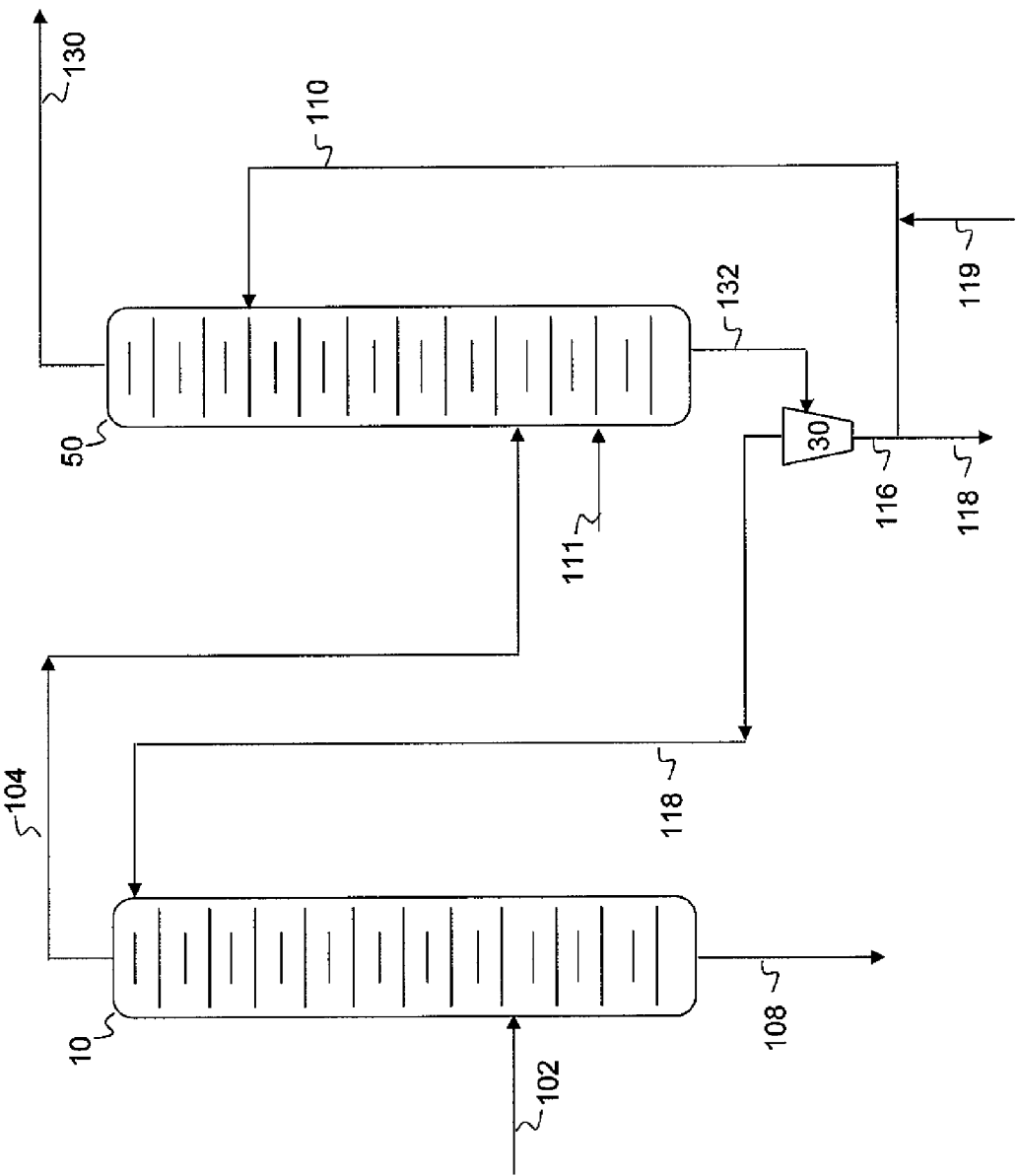
FIG. 2 is a simplified flow diagram of an alkylation process according to embodiments disclosed herein.

Various types of reactors may be used in benzene alkylation processes according to embodiments disclosed herein. Selection of the type of reactor for use in an alkylation reaction may depend on a number factors, including the desired mode of operation, throughput volume, and reaction control parameters, such as residence time and product yield. FIGS. 1 and 2 illustrate various configurations for using a slurry reactor for reformate benzene reduction.

FIG. 1 is a simplified process flow diagram for reformate benzene reduction according to embodiments disclosed herein. A full range reformate, including benzene, toluene, monoalkylate, and polyalkylate, may be fed via flow line 102 to a reformate splitter 10, where the full range reformate may be fractionated into a light reformate fraction, including benzene, and a heavy reformate fraction, including toluene, other monoalkylates, and polyalkylate existing in the reformatted feed. The light reformate may be recovered as an overheads fraction from the reformate splitter 10 via flow line 104. The heavy reformate may be recovered as a bottoms fraction from the reformate splitter 10 via flow line 108.

Alkylation catalyst fed via flow line 110 may be slurried with the overheads fraction and olefins fed via flow line 111, and the resulting slurry may be fed to flow reactor 20. Alternatively, the catalyst and reformate may be fed to flow reactor 20 separately. As illustrated in FIG. 1, flow reactor 20 may include a tubular reactor, a continuous stirred tank reactor (CSTR) or other types of flow reactors known to those skilled in the art. Conditions in flow reactor 20 are suitable for converting at least a portion of the benzene and olefins to monoalkylate. Polyalkylate and olefin oligomers may also be formed. Effluent from the flow reactor may be recovered via flow line 112, where the effluent may include monoalkylate, polyalkylate, olefin oligomers, catalyst, and unreacted olefins and benzene, if any.

The reactor effluent may be fed via flow line 112 to a separator 30 for separating the catalyst from the alkylated light reformate. A liquid fraction, comprising the monoalkylate product, unreacted benzene, polyalkylate, olefin oligomers, and unreacted olefins may be separated from the catalyst in separator 30 and recovered via flow line 114. A catalyst fraction, which may include some liquid to facilitate transport, may be recovered via line 116.

At least a portion of the catalyst fraction recovered from the separator 30 in flow line 116 may be recycled to the alkylation reactor 20 via flow line 110. Likewise, at least a portion of the catalyst fraction in flow line 116 may be purged via flow line 118, such as for regeneration or disposal. In some embodiments, the catalyst purged via flow line 118 may be fed to an FCC unit for catalyst use and/or regeneration. Make-up catalyst may be added to flow line 110 via flow line 119, or may be directly added to alkylation reactor 20.

If necessary, the liquid fraction recovered via flow line 114 may be fractionated in stripper 40 to separate any unreacted olefins or other light components or off-gas that may be contained in the reformate or olefin feeds from a light reformate product stream. The off-gas, lights, and/or unreacted olefins may be recovered from stripper 40 as an overheads fraction via flow line 120. The light reformate product stream, having a reduced benzene concentration, may be recovered from stripper 40 as a bottoms fraction via flow line 122.

Referring now to FIG. 2, where like numerals represent like parts, a process for the alkylation of benzene according to other embodiments disclosed herein is illustrated. As for the embodiment of FIG. 1, a full range reformate may be fed to a fractionator 10 to recover a heavy reformate bottoms fraction via flow line 108, including toluene and heavier components, and a light reformate overheads fraction via flow line 104, including benzene. In this embodiment, the overheads fraction is fed to a catalytic distillation column alkylation reactor 50. Alkylation catalyst may be fed to a location within column 50 such that it may become slurried with the fluid traversing downward through the column. Olefins fed via flow line 111 react with benzene in the overheads fraction fed via flow line 104 in the presence of the alkylation catalyst to form one or more of monoalkylate, polyalkylate, and olefin oligomers. Concurrently with the alkylation reaction, the monoalkylate, polyalkylate and oligomers may be separated from light components, such as any lights fed to column 50 along with the light reformate or olefin feeds, as well as unreacted olefins.

In some embodiments, unreacted benzene may also be recovered in the overheads fraction via flow line 130. In other embodiments, reactive distillation conditions may be selected so as to restrict benzene flow, essentially maintaining all unreacted benzene within column 50.

The lights fraction, including unreacted olefins, other light components, and unreacted benzene, if desired, may be recovered from reactor 50 via flow line 130. Alkylate product, including monoalkylate, polyalkylate, alkylation catalyst, and oligomers, may be recovered as a bottoms fraction via flow line 132. The catalyst may again be separated via separator 30. Additionally, the liquid alkylate product having a reduced benzene content may be used to reflux fractionator 10 or fed to fractionator 10 so as to separate unreacted benzene, if any, and to recover the alkylate product along with the heavy reformate bottoms fraction via flow line 108.

In some embodiments, the catalyst fraction recovered via flow line 118 may be fed to a fluid catalytic cracker (FCC) as equilibrium catalyst. In some embodiments, the catalyst fraction in flow line 118 may comprise of all the catalyst fraction in flow line 116, whereby the catalyst feed to alkylation reactor 50 is single pass prior to returning the catalyst to the FCC unit.

One advantage of the catalytic distillation process of FIG. 2 is that the alkylated benzene product comprising monoalkylate may be distilled out of the alkylation reaction zone and recovered as a bottoms liquid fraction to allow a higher conversion of the benzene. For example, this may mitigate a problem frequently encountered in batch and flow type reactors, where a portion of the alkylated benzene product may transalkylate to produce benzene.

The catalytic distillation process may also allow for energy savings through heat integration. For example, as described in U.S. Pat. Nos. 7,071,369 and 7,074,978, which are hereby incorporated by reference, the condensing duty of the catalytic distillation unit may be reduced by using a heavy reformate to absorb at least a portion of the light reformate product having a reduced benzene content and unreacted olefin from the overheads fraction of the catalytic distillation column.

Conventional methods for separating the catalyst fraction from the liquid fraction in the transalkylation reactor effluent may include at least one of filtration, settlement, and centrifugation or cycloning. The catalyst fraction may subsequently undergo at least one of recycling, regeneration, and disposal, where recycling and/or regeneration may be performed in a stand alone unit or may be integrated with an FCC unit.

In one embodiment the alkylation reactor effluent may be fed to a hydrocyclone separator, similar to the ones typically used in an FCC unit. Liquid and catalyst fractions including the alkylation reactor effluent enter a hydrocyclone and a vortex flow may be established, wherein a liquid fraction may be separated from a catalyst fraction, which can be separately removed. The catalyst fraction may comprise mostly the spent catalyst and at least some residual liquid from the effluent, while the liquid fraction may contain very little or no residual catalyst.

One benefit of using a heterogeneous catalyst slurry reactor over a fixed catalyst bed reactor is reduction in catalyst fouling rate due to poisoning and coking, which leads to rapid catalyst deactivation. Retardation of the catalyst deactivation rate may be achieved by maintaining at least a partial liquid level over the catalyst, for example, in a liquid slurry.

As previously stated, another benefit of a heterogeneous catalyst slurry system is that the spent or deactivated catalyst may be removed and make-up catalyst may be added without causing additional process interruptions. The ability to remove deactivated catalyst on-line eliminates the need to remove catalyst poisons from the feeds or regenerate the catalyst in a fixed bed reactor, thus reducing the cost of the benzene removal unit.

A further benefit of using a heterogeneous catalyst slurry is that an on-line regeneration system may be used to regenerate the spent catalyst from the alkylation reactor and return it back into the system, all without causing additional process interruptions. For example, a small refiner may find it economically feasible to combine the existing FCC catalyst system with a new alkylation reactor for removal of benzene from reformate, comprising using the existing FCC catalyst regeneration unit for regenerating the spent catalyst from the alkylation reactor.

Typically, the amount of spent catalyst generated by the alkylation reactor is less than the make-up requirements for the FCC unit. For example, the spent catalyst rate from the benzene alkylation unit may be in the range of 4 to 400 kg/hr. A typical FCC unit may add 100 kg/hr to 400 kg/hr or more of fresh catalyst, as based on a catalyst consumption rate from about 1 to about 5 metric tons per day.

The alkylation reaction conditions may be selected to yield the desired monoalkylate products without undue detrimental effects upon the catalyst or alkylation reactants, such as catalyst deactivation, cracking, or carbon formation. Generally, the reaction temperature may range from 100° F. to 600° F. In some embodiments, suitable operating temperature may be in the range from about 100° F. to 400° F.; from about 150° F. to about 300° F. in other embodiments. The temperature may vary depending on the reactants and product. The reaction pressure should be sufficient to maintain at least a partial liquid phase in order to retard catalyst fouling. This is typically 50 to 1000 psig, depending on the feedstock and reaction temperature. In some embodiments, operating pressures may range from about 200 to 400 psig. In a catalyst slurry flow reactor, the pressure may generally be maintained high enough to ensure minimal evaporation losses at the desired reactor operating temperature. In a catalytic distillation slurry reactor, the pressure may be maintained high enough to correspond to a boiling point within a boiling point range for the corresponding operating temperature.

In either a flow reactor or a catalytic distillation reactor, the operating temperature and pressure may be maintained to ensure that the catalyst stays wetted at all times to prevent rapid catalyst fouling and premature deactivation. Premature catalyst deactivation may significantly increase unit operating costs by one or more of: requiring more frequent replacement of spent catalyst with either fresh or regenerated catalyst; increasing unit downtime in case of fouling due to poor slurry transport; and production of undesirable impurities and other contaminants that may decrease the value of the alkylation product stream.

EXAMPLES

Example 1

300 mL of light reformate from a full range reformate and containing 14 weight percent benzene is placed in a stirred pressure vessel with 10 g crushed Beta zeolite catalyst (Zeolyst CP765 extrudate). The reactor is heated to 300° F. and propylene is added to the reactor until the reactor reaches a pressure of 150 psig. The benzene is alkylated with propylene, resulting in a light reformate containing approximately 4 weight percent benzene, indicating 70% benzene conversion.

Example 2

250 mL of neat benzene is placed in a stirred pressure vessel with 10 g of FCC catalyst (Grace Davison, OCTACAT with 50% zeolite). The reactor is heated to 300° F. and propylene is slowly added over 20 minutes until the pressure vessel reached a pressure of 145 psig. The benzene is alkylated with the propylene, resulting in a product containing 33 weight percent benzene, indicating approximately 70% benzene conversion.

Advantageously, embodiments disclosed herein may provide for reduction of benzene content in a full range reformate. The resulting liquid hydrocarbon products resulting from processes disclosed herein, having a reduced benzene content, may be readily blended into motor gasoline, while also meeting the stringent environmental and safety government regulations.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for reformate benzene reduction, the process comprising:
    feeding a light reformate fraction comprising benzene, an olefin feed, and an alkylation catalyst to an alkylation reaction zone, wherein the alkylation reaction zone comprises a slurry flow catalytic distillation column reactor;
    contacting the light reformate fraction and the olefin feed in the presence of the alkylation catalyst in the alkylation reaction zone to convert at least a portion of the benzene and the olefin to a monoalkylate;
    recovering a catalyst fraction from an alkylation reaction zone effluent; and
    recovering a light reformate product having a reduced benzene content.

2. The process according to claim 1, further comprising separating a full range reformate into at least two fractions including the light reformate fraction comprising benzene and a heavy reformate fraction comprising toluene.

3. The process according to claim 1, wherein a benzene content in the light reformate product is less than 1 weight percent.

4. The process of claim 1, wherein the olefin feed comprises a C2 to C5 olefin.

5. The process according to claim 1, wherein the olefin feed comprises at least one of an olefin and an FCC off-gas comprising an olefin.

6. The process according to claim 1, further comprising concurrently in the catalytic distillation column reactor:
contacting the benzene and the olefin feed in the presence of the alkylation catalyst to convert at least a portion of the benzene and the olefin to a monoalkylate and at least one of a polyalkylate and an olefin oligomer;
separating the light reformate from the catalyst and a heavy components comprising at least one of the polyalkylate and the olefin oligomer;
recovering the light reformate product having a reduced benzene content from the catalytic distillation column as a second overheads fraction;
recovering the catalyst and the heavy components from the catalytic distillation column as a second bottoms fraction.

7. The process according to claim 6, wherein the second overheads fraction further comprises unreacted olefin.

8. The process according to claim 7, further comprising separating the unreacted olefin from the light reformate product having a reduced benzene content.

9. The process according to claim 6, further comprising feeding the second bottoms fraction to a separation zone for separating a liquid fraction comprising the heavy components from the catalyst.

10. The process according to claim 9, further comprising feeding the liquid fraction from the separation zone to the first fractionation zone.

11. The process according to claim 1, further comprising recycling at least a portion of the recovered catalyst to the alkylation reaction zone.

12. The process according to claim 1, further comprising feeding at least a portion of the recovered catalyst to an fluid catalytic cracking (FCC) unit.

13. The process according to claim 1, where at least a portion of the catalyst feed comprises catalyst from a FCC unit.

14. The process according to claim 1, wherein the catalyst comprises zeolite particles.

15. The process according to claim 1, wherein the catalyst comprises a solid FCC zeolite catalyst.

16. The process of claim 1, further comprising blending at least one of the light reformate product and the heavy reformate to form a gasoline fuel.

17. A process for reformate benzene reduction, the process comprising:
feeding a light reformate comprising benzene, an olefin, and an alkylation catalyst to a catalytic distillation column reactor comprising an alkylation reaction zone;
concurrently in the catalytic distillation column reactor:
contacting the benzene and an olefin in the presence of the alkylation catalyst to convert at least a portion of the benzene and the olefin to a monoalkylate and at least one of a polyalkylate and an olefin oligomer;
separating the light reformate comprising the monoalkylate from the catalyst and a heavy components comprising at least one of the polyalkylate and the olefin oligomer;
recovering the heavy components and the alkylation catalyst from the catalytic distillation column as a second bottoms fraction;
recovering the light reformate having a reduced benzene content from the catalytic distillation column as a second overheads fraction;
feeding the second bottoms fraction to a separation zone for separating a liquid fraction comprising at least one of the polyalkylate and the olefin oligomer from a catalyst fraction comprising the catalyst.

18. The process of claim 17, further comprising:
feeding a full range reformate comprising benzene to a first fractionation zone;
separating the full range reformate into the light reformate comprising the benzene and a heavy reformate in the first fractionation zone.

19. The process of claim 17, further comprising feeding the liquid fraction from the separation zone to the first fractionation zone.

20. A process for reformate benzene reduction, the process comprising:
feeding a light reformate comprising benzene, an olefin-containing feed, and an alkylation catalyst to a slurry flow catalytic distillation reactor comprising an alkylation reaction zone;
contacting the benzene and the olefin in the presence of the alkylation catalyst in the alkylation reaction zone to convert at least a portion of the benzene and the olefin to a monoalkylate and at least one of a polyalkylate and an olefin oligomer;
recovering an effluent from the flow reactor comprising monoalkylate, light reformate, and the at least one of a polyalkylate and an olefin oligomer;
feeding the effluent to a separation zone for separating a liquid fraction, comprising the light reformate, monoalkylate, and the at least one of a polyalkylate and an olefin oligomer, from a catalyst fraction; and
recovering the liquid fraction as a light reformate stream having a reduced benzene content.

21. The process of claim 20, further comprising:
feeding a full range reformate comprising benzene to a first fractionation zone;
separating the full range reformate into the light reformate comprising the benzene and a heavy reformate in the first fractionation zone;
recovering the light reformate as a first overheads fraction from the first fractionation zone for the feeding a light reformate comprising benzene; and
recovering the heavy reformate as a first bottoms fraction from the first fractionation zone.

* * * * *